United States Patent
Matzinger et al.

(10) Patent No.: US 6,914,140 B1
(45) Date of Patent: Jul. 5, 2005

(54) ASYMMETRIC SYNTHESIS PROCESS

(75) Inventors: Peter Karl Matzinger, Rodersdorf (CH); Michelangelo Scalone, Birsfelden (CH); Ulrich Zutter, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 1055 days.

(21) Appl. No.: 09/546,143

(22) Filed: Apr. 10, 2000

Related U.S. Application Data

(62) Division of application No. 09/195,512, filed on Nov. 19, 1998, now Pat. No. 6,069,245, which is a continuation of application No. 08/832,253, filed on Apr. 3, 1997, now Pat. No. 5,902,882.

(30) Foreign Application Priority Data

Apr. 17, 1996  (EP) ............................................. 96105998

(51) Int. Cl.$^7$ ...................... C07D 201/16; C07D 223/08
(52) U.S. Cl. ........................................ 540/529; 540/604
(58) Field of Search ................................... 540/529, 604

(56) References Cited

U.S. PATENT DOCUMENTS 5,583,222 A * 12/1996 Barbier et al. .............. 540/596

FOREIGN PATENT DOCUMENTS

| EP | A-643 052 | 3/1995 |
| EP | A-663 393 | 7/1995 |
| WO | WO 93/03730 | 3/1993 |
| WO | WO 94/20062 | 9/1994 |
| WO | WO 97/02249 | 1/1997 |

OTHER PUBLICATIONS

Derwent Abstract 95–116733/16. 1995.
Derwent Abstract 95–247496/33, 1995.
J.W. Lampe et al., J. Org. Chem., 59, 5147–5148 (1994).
J.W. Lampe et al., J. Org. Chem., 61, 4572–4581 (1996).
Didier et al., Tetrahedron, 47(27):4941–4958 (1991).
Krogsgaard–Larsen et al., Acta Chemica Scandinavica, B32(5):327–334 (1978).
Adamset et al., J. Chem. Soc. Perkin Trans 1, pp. 2355–2362 (1995).

* cited by examiner

*Primary Examiner*—James O. Wilson
*Assistant Examiner*—Tamthom N. Truong
(74) *Attorney, Agent, or Firm*—George W. Johnston; Patricia S. Rocha-Tamaloni

(57) ABSTRACT

A novel process for the manufacture of compounds of the formula

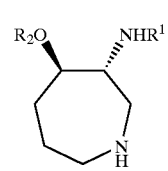

wherein $R^1$ and $R^2$ independently represent aroyl.

The present invention also concerns novel intermediates used in the novel process for making compounds of formula I.

18 Claims, No Drawings

ASYMMETRIC SYNTHESIS PROCESS

This is a divisional of application(s) Ser. No. 09/195,512 filed on Nov. 19, 1998 now U.S. Pat. No. 6,069,245 which is a continuation of Ser. No. 08/832,253 filed Apr. 3, 1997 now U.S. Pat. No. 5,902,882.

TECHNICAL FIELD

The present invention is concerned with a novel process for the manufacture of azepines and with intermediates used in this process.

DETAILED DESCRIPTION

The present invention is concerned with a process for the manufacture of azepines of the formula

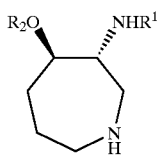

I wherein $R^1$ and $R^2$ are independently an acyl residue of an aromatic carboxylic acid.

The compounds of formula I include known, pharmacologically active compounds, for example, balanol (see Int. Patent Application WO 93/03730) and other phosphokinase inhibitors, for example, the compounds described in European Patent Application A-0 663 393. The process in accordance with the invention enables such compounds to be manufactured in a simpler and more economical manner than has been possible with previously known processes.

In the scope of the present invention, acyl residues $R^1$ and $R^2$ are selected from the group consisting of benzoic acid; benzoic acid substituted by the group selected from hydroxy, halogen, preferably fluorine, lower-alkyl and lower-alkoxy; benzoyl; and benzoyl substituted by the group selected from fluorine, lower-alkyl and lower-alkoxy. The term "lower" denotes groups with 1–6 C atoms. Compounds of formula I in which $R^2$ is p-hydroxybenzoyl or p-(2-fluoro-6-hydroxy-3-methoxybenzoyl)benzoyl and $R^1$ is p-hydroxybenzoyl or 4-hydroxy-3,5-dimethylbenzoyl are preferred. $R^4$ is an amino protecting group, perferably tert.-butoxycarbonyl.

In one embodiment of the present invention, the novel process for the manufacture of compounds of formula I comprises the catalytic asymmetric hydrogenation of a compound of the formula

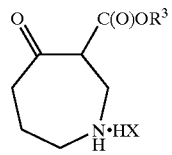

II wherein $R^3$ is lower-alkyl and HX is an acid, to a compound of the formula

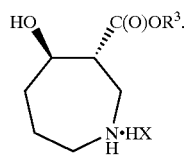

IV

Examples of acids HX for the acid addition salts of formula II and formula IV are inorganic acids, such as mineral acids, for example HCl, and organic acids, such as sulphonic acids, for example, p-toluenesulphonic acid and methanesulphonic acid.

The catalyst for the asymmetric hydrogenation is a complex of an optically active, preferably atropisomeric, diphosphine ligand with a metal of Group VIII of the periodic system, especially ruthenium. Such catalysts are described, for example, in European Patent Publication A-0 643 052.

As catalysts there come into consideration rhodium-diphosphine complexes of the formulae

| | |
|---|---|
| $(RuL)^{2+}(X^0)_2$ | III-a |
| $(RuLX^2)^{2+}(X^0)_2$ | III-b |
| $(RuLX^1X^2)^+X^3$ | III-c and |
| $RuL(X^4)_2$ | III-d | wherein $X^0$ is selected from the group consisting of $BF_4^-$, $ClO_4^-$, $B(phenyl)_4^-$, $SbF_6^-$, $PF_6^-$, and $Z^1$—$SO_3^-$;

$X^1$ is halide;

$X^2$ is benzene, hexamethylbenzene or p-cymene;

$X^3$ is selected from the group consisting of halide, $ClO_4^-$, $B(phenyl)_4^-$, $SbF_6^-$, $PF_6^-$, $Z^1$—$SO_3^-$ and $BF_4^-$;

$X^4$ is selected from the group consisting of $Z^2$—COO—, $Z^3$—$SO_3^-$, allyl and $CH_3COCH=C(CH_3)O$—;

$Z^1$ is halogenated lower alkyl or halogenated phenyl;

$Z^2$ is selected from the group consisting of lower alkyl, phenyl, halogenated lower alkyl and halogenated phenyl;

$Z^3$ is lower alkyl or phenyl; and

L is an optically active, preferably atropiso-meric, diphosphine ligand.

Especially preferred ligands L are

MeOBIPHEP (6,6'-Dimethoxybiphenyl-2,2'-diyl)bis-(diphenylphosphine);

BIPHEMP (6,6'-Dimethylbiphenyl-2,2'-diyl)bis-(diphenylphosphine);

BINAP ((1,1'-Binaphthyl)-2,2'-diyl)bis-(diphenylphosphin);

pTol-BIPHEMP (6,6'-Dimethylbiphenyl-2,2'-diyl)bis(di-(p-tolyl)phosphine);

pAn-MeOBIPHEP 6,6'-Dimethoxy-P,P,P',P'-tetrakis-(4-methoxy-phenyl)-biphenyl-2,2'-bis-phosphine;

pDMA-MeOBIPHEP 6,6'-Dimethoxy-P,P,P',P'-tetrakis-(4-dimethylamino-phenyl)-biphenyl-2,2'-bis-phosphine;

pPhenyl-MeOBIPHEP (6,6'-Dimethoxybiphenyl-2,2'-diyl)-bis(bis-(biphenyl)-phosphine);

mTol-BIPHEMP (6,6'-Dimethylbiphenyl-2,2'-diyl)bis(di-(m-tolyl)phosphine);

$Cy_2$-MeOBIPHEP P2, P2-Dicyclohexyl-6,6'-dimethoxy-P2',P2'-diphenyl-biphenyl-2,2'-bis-phosphine;

2-Furyl$_2$-BIPHEMP P,P-Diphenyl-P',P'-di-2-furyl-(6,6'-di methyl-biphenyl-2,2'-diyl)diphosphine;

(3,5-Me,4-MeO)-MeOBIPHEP 6,6'-Dimethoxy-P,P,P',P'-tetrakis-(dimethyl-4-methoxy-phenyl)-biphenyl-2,2'-bis-phosphine;

DiMeOBIPHEP (5,5',6,6'-Tetramethoxybiphenyl-2,2'-diyl) bis(diphenylphosphine);

TriMeOBIPHEP (4,4',5,5',6,6'-Hexamethoxybiphenyl-2,2'-diyl)bis(diphenylphosphine); and 2-Furyl-MeOBIPHEP (6,6'-Dimethoxybiphenyl-2,2'-diyl) bis-(di-2-furylphosphine).

These ligands are described in Patent Publications EP 643 052, EP 647 648, EP 582 692, EP 580 336, EP 690 065, EP 643 065, JP 523 9076.

Diacetoxy-ruthenium-[(R)-6,6'-dimethoxybiphenyl-2,2'-diyl]bis(diphenylphosphine [Ru(OAc)$_2$(R)-MeOBIPHEP] is an especially preferred catalyst.

The ratio of ruthenium to ligand L in the complexes of formulae II-a to III-d is from about 0.5 mol to about 2 mol, preferably at about 1 mol of ruthenium per mol of ligand. The substrate/catalyst ratio (S/C; mol/mol) is from about 20 to about 30000, preferably from about 100 to about 5000.

The hydrogenation is carried out with the exclusion of oxygen in ethanol under an elevated pressure, for example, at pressures of from about 1 bar to about 100 bar, preferably from about 5 bar to about 70 bar, and at temperatures of from about 0° C. to about 80° C., preferably from about 20° C. to about 50° C.

The compound of formula IV is converted into a carboxylic acid compound of the formula

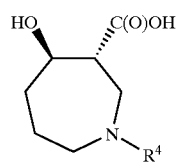

V wherein R$^4$ is a protecting group,
preferably a tert.-butoxycarbonyl group. The ester group R$^3$ of the compound of formula IV is saponified using aqueous alkali, for example, sodium hydroxide solution, at room temperature. The carboxylic acid of formula V is then converted by known methods into an acid azide or acid amide containing compound of the formula

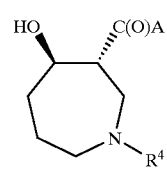

Va wherein A is azide or amino.
Subsequent degradation according to Curtius or Hofmann, yields an oxazolidone compound of the formula.

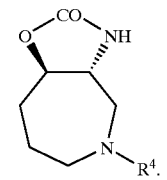

VI

The oxazolidone of formula VI is hydrolyzed to a compound having the formula

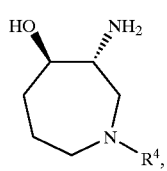

VII in a manner known per se, for example, using aqueous-alcoholic alkali while heating to 70–90° C.

The hydroxy group and the amino group in the compound of formula VII are then acylated in a manner known per se, for example, by reaction with a reactive derivative of a carboxylic acid R$^1$COOH or R$^2$COOH, such as a mixed anhydride. When these carboxylic acids contain acylatable groups, such as OH groups, these groups are conveniently intermediately protected. Compounds of formula I in which R$^1$ and R$^2$ are different from one another can be obtained, for example, by N-acylating the amino group in the compound of formula VII selectively with 1 equivalent of R$^1$COOH and subsequently O-acylating with 1 equivalent of R$^2$COOH.

The protecting group R$^4$ can be removed in a manner known per se from the compound of formula VII. For example, when R$^4$ is tert.-butoxycarbonyl group, R$^4$ can be removed by treatment with an acid, such as 2N HCl in a solvent such as ethyl acetate.

Another embodiment of the novel process for the manufacture of compounds of formula I, in accordance with the present invention, comprises microbially reducing a compound of the formula

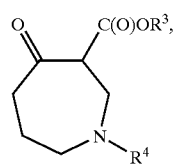

III wherein R$^3$ is lower alkyl and R$^4$ is a protecting group, to a compound having the formula

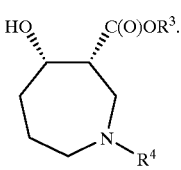

VIII

In principal, the reduction is not limited to a specific microorganism. Fungus strains (fungi), especially yeasts, are conveniently used as the microorganisms. An especially preferred microorganism is Hanseniaspora uvarum R 1052, especially the strain deposited on 16.1.1996 at the Deutschen Sammlung von Mikroorganismen und Zellkulturen (DSMZ) under No. DSM 10 496.

The reduction of a compound III to a compound of formula IV can be carried out using intact cell cultures or using enzymes obtained from the microorganisms. The preferred microorganism, Hanseniaspora uvarum R 1052, can be cultivated in aerobic aqueous submersed cultures on usual nutrient substrates which contain carbon and nitrogen sources, for example, glucose or starch, and, respectively, soya meal, yeast extract or peptone, as well as inorganic salts, such as ammonium sulphate, sodium chloride or sodium nitrate. The cultivation can be carried out at temperatures of about 20–35° C., preferably at 27° C., in a pH range of about 3–9, preferably at about pH 5–7.

The compound of formula III is added to the culture of the microorganism in an organic solvent, for example, ethyl acetate.

The course of the reduction can be followed by thin-layer chroma-tography of samples of the reaction medium. In general, the reaction takes about 8–12 hours. The reaction product, the compound of formula VIII, can be separated from the culture solution by extraction with a suitable organic solvent, for example, with ethyl acetate.

In the next reaction step, the compound of formula VIII is saponified, using aqueous alkali, for example, sodium hydroxide solution, at room temperature, to its corresponding carboxylic acid. The carboxylic acid is then converted using known methods into an acid azide or acid amide containing compound of the formula

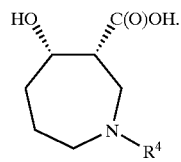
VIIIa

Subsequent degradation according to Curtius or Hofmann yields an oxazolidone compound of the formula

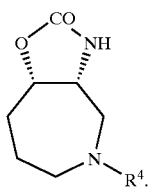
IX

By alkaline hydrolysis of the oxazolidone IX, for example by using aqueous-alcoholic alkali while heating to 70–90° C., there is obtained a compound of the formula

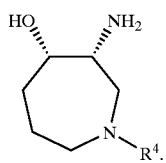
X

The hydroxy group and the amino group in the compound of formula X are then acylated in a manner known per se, for example, by reaction with a reactive derivative of a carboxylic acid $R^1$ COOH or $R^2$ COOH, such as a mixed anhydride. The compound of formula X is preferably N-acylated with an aromatic carboxylic acid of the formula $R^1$COOH to a compound having the formula

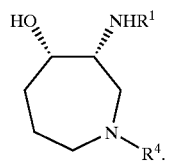
XI

The compound of formula XI is then acylated with an aromatic carboxylic acid or a reactive derivative thereof, of the formula $R^2$OH, in the presence of triphenylphosphine and diethyl azo-dicarboxylate, to yield a compound having the formula

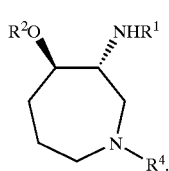
XII

The protecting group $R^4$ can be removed in a manner known per se from the compound of formula XII. For example, when $R^4$ is tert.-butoxycarbonyl group, $R^4$ can be removed by treatment with an acid, such as 2N HCl in a solvent such as ethyl acetate.

The intermediate compounds of the formulae II, IV, V, VI, VIII, VIIIa, IX, X and XI as well as the compound prepared in Example 12a and, respectively, 17 are novel and are likewise objects of the present invention.

The invention is illustrated in more detail by the following Examples, however is in no manner limited thereby. In these Examples, the abbreviations used have the following significance: "ee" is "enantiomeric excess", which is defined as percent of R-product minus percent of S-product; "dec." is "decomposition"; HPLC is high performance liquid chromatography.

EXAMPLE 1

Preparation of Compounds of Formula II and Formula III.

a) A solution of 218.3 g of di-tert-butyl dicarbonate in 250 ml of dichloromethane was added at 20–25° C. while stirring, in the course of 1 hour, to 101.2 g of piperidin-3-ol in 750 ml of dichloromethane. The reaction mixture was stirred at room temperature for a further 2 hours. Thereafter, a solution of 33.6 g of sodium bicarbonate and 11.9 g of potassium bromide in 1000 ml of deionized water was added and the reaction mixture was cooled to −20 C. After the addition of 0.39 g of 2,2,6,6-tetramethyl-piperidine 1-oxide, 560 g of 13.3% aqueous sodium hypochlorite solution were added at 0–5° C. in the course of 80 minutes. After stirring at −2° C. for a further 30 minutes, the excess sodium hypochlorite solution was added at 0–5° C. in the course of 80 minutes. After stirring at −20° C. for a further 30 minutes, the excess sodium hypochlorite was destroyed by the addition of about 10 ml of 38% aqueous sodium bisulphite solution. The reaction mixture was then warmed to 20° C. and the aqueous layer was separated and extracted with 500 ml of dichloromethane. Both organic phases were washed with 500 ml of 10% sodium chloride solution, combined and dried over sodium sulphate. After filtration and removal of the solvent under reduced pressure the oily residue was purified by distillation under reduced pressure which yielded 191.2 g of tert-butyl 3-oxo-piperidine-1-carboxylate as a colourless oil, boiling point 80–82° C./0.01 mbar.

b) 99.6 g of the compound obtained in paragraph a) were dissolved in 600 ml of diethyl ether. The solution was cooled to −70° C. and the white suspension was treated simultaneously and dropwise in the course of 1 hour with solutions of 62.0 ml of ethyl diazoacetate in 125 ml of diethyl ether and 69.0 ml of boron trifluoride etherate in 125 ml of diethyl ether, with the internal temperature being held at −70° C. After stirring at −70° C. for a further 1 hour the cooling bath was removed, the reaction mixture was warmed to 0° C. and treated with 375 ml of 10% sodium carbonate solution. The aqueous phase was separated and extracted with 250 ml of diethyl ether. The organic phases were washed with 250 ml of 10% sodium chloride solution, combined and dried over sodium sulphate. The solvent was removed under reduced pressure at 30° C. yielding ethyl 1-(tert-butoxycarbonyl)-4-oxo-azepan-3-carboxylate as a crude product in the form of a yellow oil, which was used in the next step without further purification.

c) 147.2 g of the product obtained in paragraph b) were dissolved in 1250 ml of dioxan and seeded with 0.1 g of ethyl 4-oxo-azepan-3-carboxylate hydrobromide. Thereafter, 175 ml of 5.7M. HBr/ethyl acetate were added at room temperature, while stirring, in the course of 25 minutes. After further seeding with 0.1 g of ethyl 4-oxo-azepan-3-carboxylate hydrobromide, the suspension was stirred at room temperature for 5 hours. The crystals were filtered off, washed with ethyl acetate and dried at 50° C. and 25 mbar. The resulting 91.0 g of crude ethyl 4-oxo-azepan-3-carboxylate hydrobromide was dissolved in 1250 ml of 2-butanone while stirring and heating under reflux. The solution was cooled to 65° C. and seeded with 0.1 g of pure ethyl 4-oxo-azepan-3-carboxylate hydrochloride. After cooling to room temperature, the suspension was stirred at room temperature for 1 hour and at 0° C. for 3 hours. The crystals were filtered off, washed with 200 ml of 2-butanone (cooled to −10° C.) and dried at 50° C. and 25 mbar, yielding 68.2 g of white ethyl 4-oxo-azepan-3-carboxylate hydrobromide, melting point 127–130° C. (dec.).

d) 59.4 g of the compound obtained in paragraph b) were dissolved in 1000 ml of 1M HCl in dioxan and stirred at room temperature for 24 hours. After a reaction period of 1.5 hours the solution was seeded with about 25 mg of ethyl 4-oxo-azepan-3-carboxylate hydrochloride. The white suspension was filtered, washed with dioxan and dried at 50° C. and 25 mbar, yielding 31.3 g of ethyl 4-oxo-azepan-3-carboxylate hydrochloride in the form of white crystals, which contained about 0.4 mol of dioxan per mol of hydrochloride according to the NMR spectrum. The hydrochloride was recrystallized for further purification and in order to remove the dioxan. 31.3 g of ethyl 4-oxo-azepan-3-carboxylate hydrochloride were dissolved in 600 ml of 2-butanol at 80° C. and the solution was cooled to −20° C. in the course of 2 hours and stirred at −20° C. for 3 hours. The white suspension was filtered, washed with 2-butanol (cooled to −20° C.) and dried at 50° C. and 25 mbar to yield 22.9 g of ethyl 4-oxo-azepan-3-carboxylate hydrochloride in the form of white crystals, melting point 145–148° C. (dec.).

EXAMPLE 2

75.0 g of ethyl 4-oxo-azepan-3-carboxylate hydrochloride and 800 ml of ethanol were introduced into an autoclave. The autoclave was closed and the air was removed therefrom by repeated evacuation to about 0.1 bar and pressurization with argon (7 bar) and hydrogen (40 bar) while stirring. Thereafter, a solution of 226 mg of diacetoxyrhuthenium (R)-6,6'-dimethoxybiphenyl-2,2-diyl)-bis (diphenylphosphine) in 20 ml of ethanol was fed into the autoclave at 2 bar hydrogen pressure with the exclusion of oxygen. Thereafter, hydrogen pressure was increased to 40 bar and the reaction mixture was hydrogenated while stirring at 30° C. for 19 hours and at 50° C. for 3 hours. Thereafter, the content of the autoclave was washed out with 200 ml of ethanol and the combined solutions were evaporated at 50° C./100 mbar and the brown residue was dried for 2 hours. The residue (75.9 g, consisting of about 80% 3R,4R and 20% 3S,4R isomers) was triturated with 450 ml of tetrahydrofuran at 24° C. for 19 hours and at 16° C. for 1 hour. The crystals were filtered off under suction, washed with tetrahydrofuran and dried to constant weight at 50° C./20 mbar for 3.5 hours. There were obtained 56.3 g of light beige crystals, which were again triturated with 225 ml of tetrahydrofuran as previously described. The crystals were removed by suction filtration and dried, yielding 55.1 g of ethyl (3R,4R)-4-hydroxy-azepan-3-carboxylate hydrobromide in the form of white crystals, which were enantiomerically pure according to HPLC.

EXAMPLE 3

As in Example 2, 23.2 g of ethyl 4-oxo-azepan-3-carboxylate hydrochloride in 90 ml of ethanol were hydrogenated with a solution of 36.1 mg of the ruthenium catalyst in 10 ml of ethanol under 40 bar hydrogen pressure at 30° C. for 21 hours and at 50° C. for 3 hours. The residue, consisting of about 80% 3R,4R and 20% 3S,4R isomers, was triturated with tetrahydrofuran and ethanol at 50° C. for half an hour and at room temperature for 4 hours. The crystals were filtered off under suction, washed with a small amount of tetrahydrofuran/ethanol and dried to constant weight at 50° C./20 mbar, to yield 13.3 g of enantiomerically pure ethyl (3R,4R)-4-hydroxy-azepan-3-carboxylate hydrochloride in the form of white crystals.

EXAMPLE 4

As in Example 2, 0.44 g of ethyl 4-oxo-azepan-3-carboxylate hydrochloride in 9 ml of ethanol was hydrogenated with a solution of 3.2 mg of di($\eta^2$-acetato)($\eta^4$-cycloocta-1,5-diene)-ruthenium(II) and 5.8 mg (R)-MeOBIPHEP in 1 ml of diethyl ether/THF 3/1 under 40 bar hydrogen pressure at 25° C. for 23.5 hours. The yellow hydrogenation solution was evaporated on a rotary evaporator at 40°/20 mbar. With a conversion of 83%, the residue consisted, according to HPLC analysis, of 65% ethyl (3R,4R)-4-hydroxy-azepan-3-carboxylate hydrochloride with an ee>99%.

EXAMPLE 5

The hydrogenations set forth in Table 1 were carried out in an analogous manner to Examples 2–4.

TABLE 1

Asymmetric hydrogenation of ethyl 4-oxo-azepan-3-carboxylate.HX[1)]

| Ex No | L | X | Solv. | T ° C. | Press. bar | Conv./ hr | trans[3)] % | ee | cis % | ee |
|---|---|---|---|---|---|---|---|---|---|---|
| 5a | (S)-BINAP | Cl | 2) | 25 | 40 | 62/23 | 78 | >99 | 22 | 73 |
| 5b | (R)-BIPHEMP | Cl | 2) | 25 | 40 | 90/23 | 66 | 94 | 34 | 38 |
| 5c | (R)-pTol-BIPHEMP | Cl | 2) | 25 | 40 | 93/23 | 72 | >99 | 28 | 62 |

TABLE 1-continued

Asymmetric hydrogenation of ethyl 4-oxo-azepan-3-carboxylate.HX[1])

| Ex No | L | X | Solv. | T °C. | Press. bar | Conv./hr | trans[3]) % | ee | cis % | ee |
|---|---|---|---|---|---|---|---|---|---|---|
| 5d | (R)-p-An-MeOBIPHEP | Cl | 2) | 25 | 40 | 87/23 | 80 | >99 | 20 | 77 |
| 5e | (R)-mTol-BIPHEMP | Cl | 2) | 25 | 40 | 90/24 | 58 | 97 | 42 | 47 |
| 5f | (R)-pDMA-MeOBIPHEP | Cl | 2) | 25 | 40 | 79/24 | 72 | >99 | 28 | 95 |
| 5g | (R)-pPhenyl-MeOBIPHEP | Cl | 2) | 25 | 40 | 54/23 | 82 | >99 | 18 | 26 |
| 5h | (S)-3,5-Me,4-MeO-MeOBIPHEP | Cl | 2) | 25 | 40 | 34/23 | 55 | >99 | 45 | 61 |
| 5i | (R)-DiMeOBIPHEP | Cl | 2) | 25 | 40 | 99/23 | 66 | >99 | 34 | 86 |
| 5j | (R)-MeOBIPHEP | Br | EtOH | 40 | 100 | 99/21 | 76 | >99 | 24 | 84 |
| 5k | " | Br | EtOH | 60 | 100 | 100/21 | 69 | >99 | 31 | 85 |
| 5l | (R)-2-Furyl-MeOBIPHEP | Br | EtOH | 40 | 100 | 76/29 | 64 | 98 | 36 | 95 |
| 5m | (R)-2-Furyl-2-Biphemp | Br | EtOH | 40 | 100 | 94/21 | 68 | >99 | 32 | 69 |
| 5n | (R)-TriMeOBIPHEP | Br | EtOH | 30 | 100 | 100/23 | 76 | >99 | 24 | 95 |
| 5o | (R)-Cy2-MeOBIPHEP | Cl | EtOH | 80 | 20 | 100/22 | 38 | >99 | 62 | 92 |
| 5p | (R)-MeOBIPHEP | Cl | MeOH | 30 | 100 | 100/22 | 75 | >99 | 25 | 88 |
| 5q | " | Cl | iPrOH | " | " | 90/22 | 78 | >99 | 22 | 84 |
| 5r | " | Cl | AcOH | 25 | 40 | 97/23 | 5 | >99 | 95 | 94 |

1) Catalyst preparation analogously to Example 2 and 3.
2) Catalyst preparation: in situ analogously to Example 4, solvent: ethanol-diethyl ether-tetrahydrofuran 9:0.65:0.35.
3) trans: compound IV or its enantiomer. Chiral diphosphine ligands with (R)-configuration give (3R,4R)-IV.

EXAMPLE 6

As in Example 3, 3.32 g of ethyl 4-oxo-azepan-3-carboxylate hydrochloride were hydrogenated in the presence of 6.3 mg of [RuCl((R)-MeOBIPHEP)(C6H6)]Cl under 40 bar hydrogen pressure at 30° C. for 19 hours and at 50° for 3 hours. The yellow hydrogenation solution was evaporated on a rotary evaporator at 40°/20 mbar. With a conversion of 95% the residue consisted, according to HPLC analysis, of 79% ethyl (3R,4R)-4-hydroxy-azepan-3-carboxylate with an ee>99%.

EXAMPLE 7

A catalyst solution was prepared in a glove box ($O_2$ content <1 ppm) by dissolving 1.3 ml of a 0.03 molar ethanolic HBr solution and 16.1 mg of Ru(OAc)2((R)-MeOBIPHEP) in 10 ml of ethanol and stirring for 0.5 hour. Then, 0.53 g of ethyl 4-oxo-azepan-3-carboxylate hydrobromide and 2 ml of the catalyst solution prepared above were placed in 4 ml of ethanol in an autoclave and hydrogenated at 20° C. under 100 bar hydrogen pressure for 21 hours. The yellow hydrogenation solution was evaporated on a rotary evaporator at 40°/20 mbar. With a conversion of 76%, the residue consisted, according to HPLC analysis, of 58% ethyl (3R,4R)-4-hydroxy-azepan-3-carboxylate hydrobromide with an ee>99%.

EXAMPLE 8

A catalyst solution was prepared in a glove box ($O_2$ content <1 ppm) by dissolving 1.0 ml of a 0.04 molar ethanolic HBF4 solution and 32.1 mg of Ru(OAc)2((R)-MeOBIPHEP) in 10 ml of ethanol and stirring for 0.5 hour. Then, 0.53 g of ethyl 4-oxo-azepan-3-carboxylate hydrobromide and 1 ml of the catalyst solution prepared above were placed in 9 ml of ethanol in an autoclave and hydrogenated at 20° C. under 100 bar hydrogen pressure for 21 hours. The yellow hydrogenation solution was evaporated on a rotary evaporator at 40°/20 mbar. With a conversion of 44% the residue consisted according to HPLC analysis of 37% ethyl (3R,4R)-4-hydroxy-azepan-3-carboxylate hydrobromide with an ee>99%.

EXAMPLE 9

67.0 g of ethyl (3R,4)-4-hydroxy-azepan-3-carboxylate hydrobromide were suspended in 500 ml of tert-butyl methyl ether and treated with 30.4 g of triethylamine. Thereafter, a solution of 54.6 g of di-tert-butyl dicarbonate in 25 ml of tert-butyl methyl ether was added at room temperature in the course of 20 minutes. Thereafter, the mixture was stirred at room temperature for a further 2 hours.

500 ml of 2N NaOH were added to the white suspension and the reaction mixture was stirred vigorously at room temperature for 2 hours. The reaction mixture was then acidified with 175 ml of 6N HCl and, after phase separation, the aqueous phase was extracted twice with 100 ml of tert-butyl methyl ether. All organic phases were washed with 150 ml of 10% sodium chloride solution, combined and dried over sodium sulphate. After removal of the solvent under reduced pressure at 40° C. the crude hydroxyacid was dissolved in 260 ml of butyl acetate at about 85° C. After seeding with pure product the suspension was cooled to −20° C. in the course of 2 hours and stirred at this temperature overnight. The suspension was filtered, washed with 100 ml of hexane and dried at 50° C. and 25 mbar, yielding 55.9 g of (3R,4R)-4-hydroxy-azepan-1,3-dicarboxylic acid 1-tert-butyl ester, melting point 121.5–122.5° C.

EXAMPLE 10

300 ml of ethyl acetate and 20.9 ml of triethylamine were added to 38.9 g of the compound prepared in Example 9.

The solution was heated to reflux, then 32.4 ml of diphenylphosphoryl azide were added in the course of 30 minutes and the heating under reflux was continued for a further 2 hours. After cooling to room temperature the reaction mixture was treated with 300 ml of ethyl acetate and washed with 150 ml of 5% sodium hydrogen carbonate solution and twice with 150 ml of water. The aqueous phases were extracted twice with 300 ml of ethyl acetate. The combined organic phases were dried over sodium sulphate and evaporated at 45° C. under reduced pressure. The crude crystalline residue was dissolved in 300 ml of butyl acetate, seeded with pure product, cooled to −20° C. in the course of about 3 hours and stirred overnight. The suspension was filtered, washed with butyl acetate (pre-cooled to −20° C.) and dried at 60° C. and 25 mbar to yield 29.9 g of (3aR,8aR)-5-tert-butoxycarbonyl-2-oxo-octahydro-oxazolo[4,b-c]azepine, melting point 152.5–153.5° C.

EXAMPLE 11

25.6 g of the compound prepared in Example 10 were added to 250 ml of methanol and 250 ml of 2N NaOH. The reaction mixture was heated to reflux and held at this temperature for 3 hours. After cooling, 265 ml of solvent were distilled off at 50° C. and 150 mbar and the residue was extracted three times with 200 ml of ethyl acetate each time. The three organic phases were washed with 50 ml of 10% sodium chloride solution, combined and dried over sodium sulphate. After removal of the solvent the viscous oil obtained as the residue was dissolved in 100 ml of cyclohexane at 60° C., seeded with pure product, cooled to room temperature in the course of 2 hours and stirred overnight. The suspension was filtered, washed with 40 ml of cyclohexane and dried at 50° C. and 25 mbar, yielding 21.5 g of tert-butyl (3R,4R)-3-amino-4-hydroxy-azepan-1-carboxylate, melting point 99–100.5° C.

EXAMPLE 12 a) 4.58 g of p-toluenesulphonyl chloride dissolved in 24 ml of dichloromethane were added at room temperature in the course of 10 minutes to 4.66 g of 4-tert-butoxybenzoic acid and 6.11 g of 4-dimethylaminopyridine in 30 ml of dichloromethane. After stirring at room temperature for 2 hours, 2.30 g of the compound prepared in Example 6 in 6 ml of dichloromethane were added in the course of 10 minutes. Thereafter, the mixture was stirred at room temperature for 16 hours. The reaction mixture was washed twice with 20 ml of 1N NaOH each time and then with 40 ml of 1N HCl and 40 ml of water. All aqueous phases were extracted with 20 ml of dichloromethane. The combined organic phases were dried over sodium sulphate and the solvent was removed under reduced pressure. The residual white foam was chromatographed over 300 g of silica gel with 6.5 l of hexane-ethyl acetate (2:1). Fractions of 250 ml were collected. Fractions 8–25 were combined and the solvent was evaporated under reduced pressure, there being obtained 5.91 g of a white foam which was dissolved in 80 ml of heptane at 60° C. After stirring at −20° C. overnight the crystals were filtered off, washed with cold heptane and dried at 50° C. and 25 mbar to yield 5.34 g of tert-butyl (3R,4R)-3-(4-tert-butoxy-benzoylamino)-4-(4-tert-butoxy-benzoyloxy)-azepan-1-carboxylate, melting point 1 25.5–127.5° C.

b) 20.0 ml of 5M HCl in ethyl acetate were added at room temperature and while stirring to 5.83 g of the compound obtained in paragraph a) dissolved in 30 ml of ethyl acetate. The reaction mixture was stirred at room temperature overnight and the white precipitate was filtered off and washed three times with 5 ml of ethyl acetate each time and dried at 50° C./25 mbar for 16 hours. The white powder obtained was dissolved in 50 ml of water and stirred at 50° C. for 1 hour. The solution was then lyophilized and yielded 3.97 g of pure 3-(4-hydroxy-benzoylamino)-4-(4-hydroxy-benzoyloxy)-hexahydroazepine hydrochloride.

EXAMPLE 13

Hanseniaspora uvarum R 1052 was cultivated for 3 days at 27° C. in a Petri dish containing a solid nutrient substrate. After 3 days, 100 ml of liquid nutrient medium in a 500 ml shaking flask was seeded with a loop of this culture. This pre-culture was shaken at 27° C. for 18 hours. The cells grew to a density of $5 \times 10^8$ cells/ml (stationary phase). The entire pre-culture was used to inoculate a reactor which contained 7500 ml of nutrient medium (containing 1% yeast extract Difco: Bacto Yeast Extract # 0127-17-9, 1% Pepton Difco: Bacto Peptone # 0118-17-0 and 2% glucose in deionized water). After 18 hours, 750 ml of 50% glucose solution and immediately thereafter 29 g of the compound prepared in Example 1b dissolved in 20 ml of ethyl acetate were added in the course of 25 minutes. After 12 hours the culture solution was extracted twice with 2000 ml of ethyl acetate each time. The combined organic phases were dried over sodium sulphate. The solvent was removed under reduced pressure at 30° C. to yield 30.1 g of ethyl (3R,4S)-1-(tert-butoxycarbonyl)-4-hydroxy-azepan-3-carboxylate as a viscous orange oil.

EXAMPLE 14 a) A mixture of 28.7 g of the compound prepared in Example 13 in 200 ml of tert-butyl methyl ether and 200 ml of 2N NaOH was stirred vigorously at room temperature for 4 hours and then at 50° C. for 20 hours. After cooling, the aqueous phase was extracted twice with 100 ml of tert-butyl methyl ether each time. The organic phases were discarded. The aqueous phase was acidified cautiously with about 70 ml of 6N HCl and extracted once with 200 ml of tert-butyl methyl ether and twice with 100 ml of tert-butyl methyl ether each time. All three organic phases were washed once with 50 ml of 10% sodium chloride solution, combined and dried over sodium sulphate. After removal of the solvent under reduced pressure (40° C./25 mbar) the brown viscous oil was dissolved in 60 ml of isopropyl ether at 60° C. and left to crystallize at −20° C. for 16 hours. The crystals were filtered off, washed with a small amount of isopropyl ether, cooled to −20° C. and dried at 40° C. for 5 hours and 25 mbar, yielding 12.0 g of (3R,4S)-4-hydroxy-azepan-1,3-dicarboxylic acid 1-tert-butyl ester of melting point 98.5–101.5° C.

b) 140 ml of ethyl acetate, 9.8 ml of triethylamine and 15.9 ml of diphenylphosphoryl azide were added to 18.1 g of the compound obtained in paragraph a). The solution was heated to reflux for 2 hours, cooled, diluted with 140 ml of ethyl acetate and washed with 70 ml of 5% sodium hydrogen carbonate solution and twice with 70 ml of water each time. The three aqueous phases were separated and washed three times with 140 ml of ethyl acetate. The combined organic phases were dried over sodium sulphate and the solvent was removed at 45° C./25 mbar. The crude crystalline residue was dissolved in 140 ml of butyl acetate at about 80° C., seeded with pure product, cooled and stirred at −20° C. for 6 hours. The suspension was filtered, washed with butyl acetate (cooled to −20° C.) and dried at 60° C. and 25 mbar overnight, to yield 13.3 g of tert-butyl (3aR,8aS)-2-oxo-octahydro-oxazolo[4,b-c] azepine-5-carboxylate of melting point 158–159° C.

EXAMPLE 15

200 ml of methanol and 200 ml of 2N NaOH were added to 20.5 g of the compound prepared in Example 14b). The reaction mixture was heated to reflux and left at this temperature for 4 hours. After cooling, 200 ml of methanol were distilled off at 50° C. and 150 mbar and the residue was extracted three times with 160 ml of ethyl acetate each time. The organic phases were washed with 40 ml of 10% sodium chloride solution, combined and dried over sodium sulphate. After removal of the solvent, the viscous oil obtained as the residue was dissolved in 80 ml of methylcyclohexane at 50° C., seeded with pure product, cooled and stirred at 0° C. for 4 hours. The crystals were filtered off, washed with 20 ml of methylcyclohexane and dried at 50° C. and 25 mbar overnight, yielding 17.4 g of tert-butyl (3R,4S)-3-amino-4-hydroxy-azepan-1-carboxylate, melting point 64–67° C.

EXAMPLE 16

9.06 g of p-toluenesulphonyl chloride in 75 ml of dichloro-methane were added at room temperature to 11.5 g of 4-(tert-butoxy)-benzoic acid and 13.1 g of 4-dimethylaminopyridine in 100 ml of dichloromethane. The reaction mixture was stirred for a further 2 hours. The solution was then added in the course of 1 hour to 11.5 g of the compound prepared in Example 10 dissolved in 50 ml of dichloromethane. After stirring at room temperature for 1 hour, the reaction mixture was washed with 100 ml of 1N NaOH, 100 ml of 1N HCl and 100 ml of water. All aqueous phases were extracted with 50 ml of dichloromethane. The combined organic phases were dried over sodium sulphate and the solvent was separated under reduced pressure. The foam-like residue was dissolved in 400 ml of hot heptane and left to crystallize at room temperature overnight. The crystals were washed with 25 ml of heptane and dried at 50°/25 mbar to yield 17.3 g of tert-butyl (3R,4S)-3-(4-tert-butoxy-benzoylamino)-4-hydroxy-azepan-1-carboxylate of melting point 131.5–132.5° C.

EXAMPLE 17

262 mg of diethyl azadicarboxylate in 2 ml of tetrahydrofuran were added while stirring to 407 mg of the compound prepared in Example 16, 253 mg of 4-(tert-butoxy)-benzoic acid and 394 g of triphenylphosphine in 8 ml of tetrahydrofuran. After stirring at 50° C. for 4 hours, the solvent was removed under reduced pressure and the residue was taken up in 20 ml of cyclohexane and washed once with 20 ml of water and twice with 10 ml of 70% methanol/water each time. The aqueous-alcoholic phase was extracted twice with 10 ml of cyclohexane each time. The combined cyclohexane phases were dried over sodium sulphate and the solvent was removed under reduced pressure. The residual viscous oil was dissolved in 10 ml of hot heptane, seeded with pure end product and left to crystallize at room temperature for 18 hours and yielded 241 mg of tert-butyl (3R,4R)-3-(4-tert-butoxy-benzoylamino]-4-(4-tert-butoxy-benzoyloxy)-azepan-1-carboxylate of melting point 126–128° C. This compound can be reacted further as in Example 12b.

EXAMPLE 18

12.91 g of p-toluenesulphonyl chloride dissolved in 15 ml of dichloromethane were added at room temperature in the course of 15 minutes to 1.94 g of 4-(tert-butoxy)-benzoic acid and 2.63 g of 4-dimethylaminopyridine in 20 ml of dichloromethane. The reaction mixture was stirred for 2 hours and added in the course of 1 hour to 2.30 g of tert-butyl (3R,4R)-3-amino-4-hydroxy-azepan-1-carboxylate dissolved in 10 ml of dichloromethane. After stirring for 1 hour the reaction mixture was washed with 20 ml of 1N NaOH, 20 ml of 1N HCl and 20 ml of water. All aqueous phases were washed in succession with 10 ml of dichloromethane. The combined organic phases were dried over sodium sulphate, filtered and the solvent was evaporated. The foam-like residue obtained was dissolved in 80 ml of hot heptane and crystallized at room temperature overnight. The crystals were washed with 10 ml of heptane and dried to yield 3.23 g of tert-butyl (3R,4R)-3-(4-tert-butoxy-benzoylamino)-4-hydroxy-azepan-1-carboxylate, m.p. 134–135° C.

EXAMPLE 19

572 mg of p-toluenesulphonyl chloride in 3.5 ml of dichloromethane were added at room temperature in the course of 10 minutes to 679 mg of 4-benzoyl-benzoic acid and 764 mg of 4-dimethylaminopyridine in 5 ml of dichloromethane. After further stirring at room temperature for 2 hours 1016 mg of tert-butyl (3R,4R)-3-(4-tert-butoxy-benzoylamino)-4-hydroxy-azepan-1-carboxylate in 2.5 ml of dichloromethane were added in the course of 10 minutes while stirring. Thereafter, the reaction mixture was stirred at room temperature for a further 2.5 hours and washed with 6 ml of 1N NaOH, 6 ml of 1N HCl and 6 ml of water. All aqueous phases were extracted in succession with 6 ml of dichloromethane. The combined organic phases were dried over sodium sulphate and the solvent was evaporated. The crude product was chromatographed over 100 g of silica gel with 1.41 of hexane/ethyl acetate (2:1). Fractions of 100 ml were collected. Fractions 5–9 were combined and the solvent was evaporated. There were obtained 1.48 g of a white foam, which was crystallized from 50 ml of hot heptane, to yield 1.24 g of tert-butyl (3R,4R)-3-(4-tert-butoxy-benzoylamino)-4-(4-benzoyl-benzoyloxy)-azepan-1-carboxylate, m.p. 145–148° C., as a white powder.

EXAMPLE 20

3.0 ml of 5N HCl in ethyl acetate were added at room temperature while stirring to 922 mg of the azepine prepared in Example 19 in 4.0 ml of ethyl acetate. The reaction mixture was stirred at room temperature overnight and the precipitate was filtered off, washed three times with 2 ml of ethyl acetate and dried at 50° C./25 mbar for 16 hours yielding 0.70 g of 3-(4-hydroxy-benzoylamino)-4-(4-benzoyl-benzoyloxy)-hexahydroazepine hydrochloride.

What is claimed is:

1. A compound selected from the group consisting of compounds of the formula

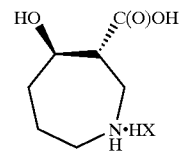

IV wherein $R^3$ is lower alkyl and HX is an acid.

2. The compound of claim 1, wherein the compound is ethyl (3R,4R)-4-hydroxy-azepan-carboxylate hydrochloride.

3. A compound selected from the group consisting of compounds of the formula

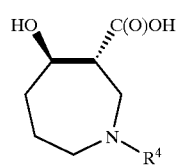

V wherein $R^4$ is an amino-protecting group.

4. The compound of claim 3, wherein the compound is (3R,4R)-4-Hydroxy-azepan-1,3-dicarboxylic acid 1-tert.-butyl ester.

5. A compound selected from the group consisting of compounds of the formula

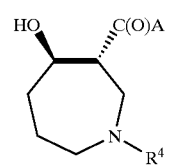

Va wherein A is azido or amino and $R^4$ is an amino-protecting group.

6. A compound selected from the group consisting of compounds of the formula

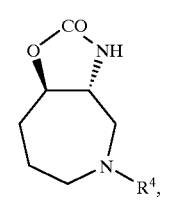

VI wherein $R^4$ is an amino-protecting group.

7. The compound of claim 6, wherein the compound is (3aR,8aR)-5-tert-Butoxycarbonyl-2-oxo-octahydro-oxazolo(4,b-c)azepine.

8. A compound selected from the group consisting of compounds of the formula

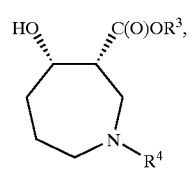

VIII wherein $R^3$ is lower alkyl and $R^4$ is an amino-protecting group in the absence of substantial amounts of other enantiomers of the compound.

9. The compound of claim 8, wherein the compound is ethyl (3R,4S)-1-(tert-butoxycarbonyl)-4-hydroxy-azepan-3-carboxylate.

10. A compound selected from the group consisting of compounds of the formula

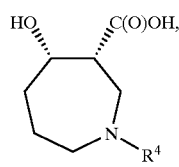

VIIIa wherein $R^4$ is an amino-protecting group.

11. The compound of claim 10, wherein the compound is (3R,4S)-4-Hydroxy-azepan-1,3-dicarboxylic acid 1-tert-butyl ester.

12. A compound selected from the group consisting of compounds of the formula

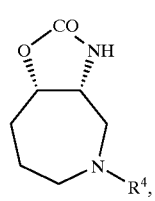

IX wherein $R^4$ is an amino-protecting group.

13. The compound of claim 12, wherein the compound is tert.Butyl (3aR,8aS)-2-oxo-octahydro-oxazolo(4,b-c)azepine-5-carboxylate.

14. A compound selected from the group consisting of compounds of the formula

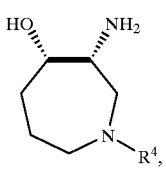

X wherein $R^4$ is an amino-protecting group.

15. The compound of claim 14, wherein the compound is tert-Butyl (3R,4S)-3-amino-4-hydroxy-azepan-1-carboxylate.

16. A compound selected from the group consisting of compounds of the formula

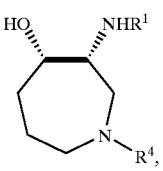

XI wherein $R^1$ is an acyl residue of an aromatic carboxylic acid and $R^4$ is an amino-protecting group.

17. The compound of claim 16, wherein the compound is tert-Butyl (3R,4S)-3-(4-tert-butoxy-benzoylamino)-4-hydroxy-azepan-1-carboxylate.

18. The compound tert-Butyl (3R,4R)-3-(4-tert-butoxy-benzoylamino)-4-(4-tert-butoxy-benzoyloxy)-azepan-1-carboxylate.

* * * * *

UNITED STATES PATENT AND TRADEMARK OFFICE
CERTIFICATE OF CORRECTION

PATENT NO.    : 6,914,140 B1
DATED         : July 5, 2005
INVENTOR(S)   : Matzinger et al.

It is certified that error appears in the above-identified patent and that said Letters Patent is hereby corrected as shown below:

Column 14,
Lines 55-63, Formula IV reads " 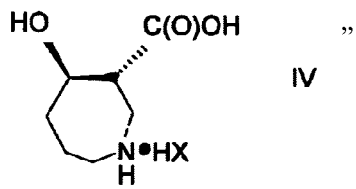 "

and should read -- 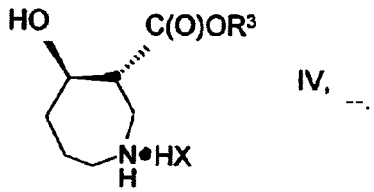 --.

Signed and Sealed this

Twenty-second Day of November, 2005

JON W. DUDAS
*Director of the United States Patent and Trademark Office*